US012629042B2

(12) United States Patent
De Haan et al.

(10) Patent No.: US 12,629,042 B2
(45) **Date of Patent: *May 19, 2026**

(54) DEVICE, SYSTEM AND METHOD FOR OBTAINING A VITAL SIGNAL OF A SUBJECT

(71) Applicant: KONINKLIJKE PHILIPS N.V., Eindhoven (NL)

(72) Inventors: Gerard De Haan, Helmond (NL); Albertus Cornelis Den Brinker, Eindhoven (NL); Wenjing Wang, Utrecht (NL)

(73) Assignee: Koninklijke Philips N.V., Eindhoven (NL)

( * ) Notice: Subject to any disclaimer, the term of this patent is extended or adjusted under 35 U.S.C. 154(b) by 658 days.

This patent is subject to a terminal disclaimer.

(21) Appl. No.: 17/508,127

(22) Filed: Oct. 22, 2021

(65) Prior Publication Data

US 2022/0039678 A1 Feb. 10, 2022

Related U.S. Application Data

(63) Continuation of application No. 16/339,793, filed as application No. PCT/EP2017/076947 on Oct. 23, 2017, now Pat. No. 11,154,209.

(30) Foreign Application Priority Data

Oct. 27, 2016 (EP) ..................................... 16195967

(51) Int. Cl.
| A61B 5/024 | (2006.01) |
| A61B 5/00 | (2006.01) |
| A61B 5/1495 | (2006.01) |

(52) U.S. Cl.
CPC ........ *A61B 5/02416* (2013.01); *A61B 5/1495* (2013.01); *A61B 5/7207* (2013.01); *A61B 5/7257* (2013.01)

(58) Field of Classification Search
CPC . A61B 5/02416; A61B 5/7207; A61B 5/7257; A61B 5/145; A61B 5/11; A61B 5/0075
See application file for complete search history.

(56) References Cited

U.S. PATENT DOCUMENTS

| 9,986,922 B2 | 6/2018 | Uchida | |
| 2013/0271591 A1* | 10/2013 | Van Leest | ............ A61B 5/7207 |
| | | | 348/77 |
| 2014/0275825 A1* | 9/2014 | Lisogurski | ......... A61B 5/14552 |
| | | | 600/323 |

FOREIGN PATENT DOCUMENTS

| WO | 2013027027 | 2/2013 |
| WO | 2013/038326 | 3/2013 |

(Continued)

OTHER PUBLICATIONS

Xiong, et al: "Spectral Matrix Decomposition-Based Motion Artifacts Removal in Multi-Channel PPG Sensor Signals", IEEE Access, vol. 4, Jun. 7, 2016.

(Continued)

*Primary Examiner* — Abid A Mustansir

(57) ABSTRACT

In an approach to obtaining vital signs of a subject, a subject monitoring device obtains at least two detection signals acquired from a subject that are related to a physiological property of the subject and allows extraction of a vital sign of the subject. The subject monitoring device performs a spectral decomposition of the at least two detection signals to obtain two or more spectral components of the detection signals and determines a weight per spectral component based on an estimate of the relevance. The subject monitoring device determines a weight value by determining at (Continued)

least one of a variance of the spectral component and a standard deviation of the spectral component and determines whether at least one of the variance and the standard deviation exceed a predetermined limit. Responsive to determining that at least one of the variance and the standard deviation do not exceed the predetermined limit, the subject monitoring device setts the weight to a weight value of 1 and extracts the weighted vital sign of the subject.

20 Claims, 4 Drawing Sheets

(56) References Cited

FOREIGN PATENT DOCUMENTS

| | | |
|---|---|---|
| WO | 2015049150 | 3/2013 |
| WO | 2014141084 | 9/2014 |
| WO | 2015132063 A1 | 9/2015 |
| WO | 2015/180986 | 12/2015 |

OTHER PUBLICATIONS

Krishnan, et al: "Motion Artifact Reduction in Photopleythysmography Using Magnitude-Based Frequency Domain Independent Component Analysis", Computer Communications and Networks, 2008. ICCCN '08. Proceedings of 17th International Conference On, IEEE, Piscataway, NJ, USA, Aug. 3, 2008.

Verkruysse, et al: "Remote plethysmographic imaging using ambient light", Opt Express. Dec. 22, 2008; 16(26): 21434-21445.

Van Gastel, et al: "Motion robust remote-PPG in infrared", IEEE Transactions on Biomedical Engineering, vol. 62, No. 5, May 2015.

De Haan, et al: "Improved motion robustness of remote-PPG by using the blood volume pulse signature", Physiol Meas. Aug. 27, 2014;35(9):1913-1926.

De Haan, et al: "Robust pulse-rate from chrominance-based rPPG", IEEE Transactions on Biomedical Engineering, vol. 60, No. 10, Oct. 2013.

* cited by examiner

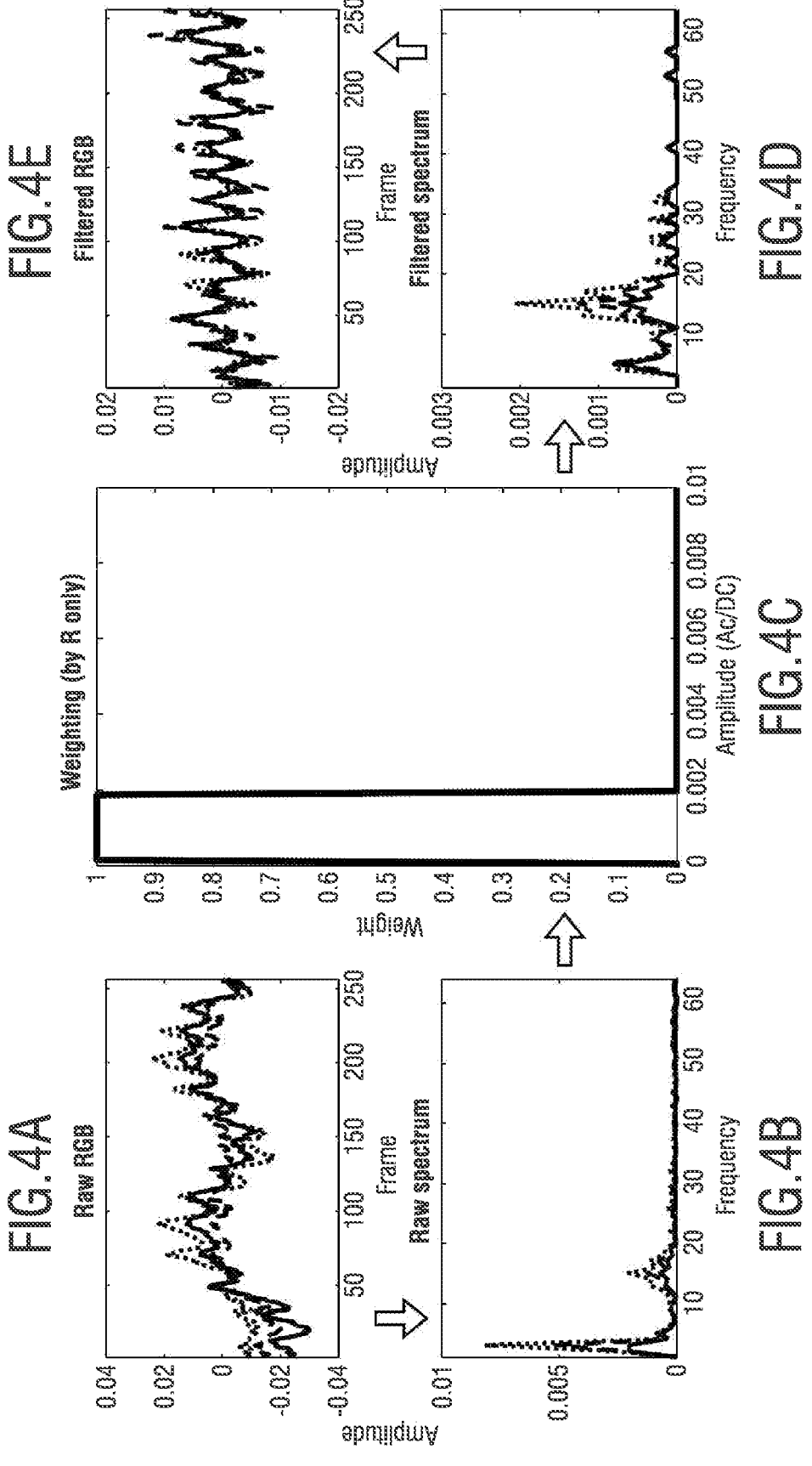

DEVICE, SYSTEM AND METHOD FOR OBTAINING A VITAL SIGNAL OF A SUBJECT

CROSS REFERENCE TO RELATED APPLICATION

The present application is a continuation of co-pending U.S. patent application Ser. No. 16/339,793, filed Apr. 5, 2019, which is the U.S. National Phase application under 35 U.S.C. § 371 of International Application No. PCT/EP2017/076947 filed Oct. 23, 20217, which claims the benefit of International Application No. 16195967.1 filed Oct. 27, 2016. These applications are hereby incorporated by reference herein.

FIELD OF THE INVENTION

The present invention relates to a device, system and method for obtaining a vital signal of a subject.

BACKGROUND OF THE INVENTION

Vital signs of a person, for example the heart rate (HR), the respiration rate (RR) or the arterial blood oxygen saturation, serve as indicators of the current state of a person and as powerful predictors of serious medical events. For this reason, vital signs are extensively monitored in inpatient and outpatient care settings, at home or in further health, leisure and fitness settings.

One way of measuring vital signs is plethysmography. Plethysmography generally refers to the measurement of volume changes of an organ or a body part and in particular to the detection of volume changes due to a cardio-vascular pulse wave traveling through the body of a subject with every heartbeat.

Photoplethysmography (PPG) is an optical measurement technique that evaluates a time-variant change of light reflectance or transmission of an area or volume of interest. PPG is based on the principle that blood absorbs light more than surrounding tissue, so variations in blood volume with every heart beat affect transmission or reflectance correspondingly. Besides information about the heart rate, a PPG waveform can comprise information attributable to further physiological phenomena such as the respiration. By evaluating the transmittance and/or reflectivity at different wavelengths (typically red and infrared), the blood oxygen saturation can be determined.

Conventional pulse oximeters (also called contact PPG device herein) for measuring the heart rate and the (arterial) blood oxygen saturation (also called SpO2) of a subject are attached to the skin of the subject, for instance to a fingertip, earlobe or forehead. Therefore, they are referred to as 'contact' PPG devices. A typical pulse oximeter comprises a red LED and an infrared LED as light sources and one photodiode for detecting light that has been transmitted through patient tissue. Commercially available pulse oximeters quickly switch between measurements at a red and an infrared wavelength and thereby measure the transmittance of the same area or volume of tissue at two different wavelengths. This is referred to as time-division-multiplexing. The transmittance over time at each wavelength gives the PPG waveforms for red and infrared wavelengths. Although contact PPG is regarded as a basically non-invasive technique, contact PPG measurement is often experienced as being unpleasant and obtrusive, since the pulse oximeter is directly attached to the subject and any cables limit the freedom to move and might hinder a workflow. The same holds for contact sensors e.g. for respiration, SpO2 or heart rate measurements, which may sometimes be practically impossible because of extremely sensitive skin (e.g. of patients with burns and preterm infants).

Recently, non-contact, remote PPG (rPPG) devices (also called camera rPPG device herein) for unobtrusive measurements have been introduced. Remote PPG utilizes light sources or, in general radiation sources, disposed remotely from the subject of interest. Similarly, also a detector, e.g., a camera or a photo detector, can be disposed remotely from the subject of interest. Therefore, remote photoplethysmographic systems and devices are considered unobtrusive and well suited for medical as well as non-medical everyday applications. However, remote PPG devices typically achieve a lower signal-to-noise ratio.

Verkruysse et al., "Remote plethysmographic imaging using ambient light", Optics Express, 16(26), 22 Dec. 2008, pp. 21434-21445 demonstrates that photoplethysmographic signals can be measured remotely using ambient light and a conventional consumer level video camera, using red, green and blue color channels.

Using PPG technology, vital signs can be measured, which are revealed by minute light absorption changes in the skin caused by the pulsating blood volume, i.e. by periodic color changes of the human skin induced by the blood volume pulse. As this signal is very small and hidden in much larger variations due to illumination changes and motion, there is a general interest in improving the fundamentally low signal-to-noise ratio (SNR). There still are demanding situations with severe motion and/or challenging environmental illumination conditions, particularly occurring in heart-rate monitoring in a fitness setting, or with a high required accuracy of the application, where an improved robustness and accuracy of the vital sign measurement devices and methods is required, which is typical for the more critical healthcare applications.

To achieve motion robustness, pulse-extraction methods profit from the color variations having an orientation in the normalized RGB color space which differs from the orientation of the most common distortions usually induced by motion. A known method for robust pulse signal extraction uses the known fixed orientation of the blood volume pulse in the normalized RGB color space to eliminate the distortion signals. Further background is disclosed in M. van Gastel, S. Stuijk and G. de Haan, "Motion robust remote-PPG in infrared", IEEE, Tr. On Biomedical Engineering, Vol. 62, No. 5, 2015, pp. 1425-1433, and in G. de Haan and A. van Leest, "Improved motion robustness of remote-PPG by using the blood volume pulse signature", Physiol. Meas. 35 1913, 2014, which describes that the different absorption spectra of arterial blood and bloodless skin cause the variations to occur along a very specific vector in a normalized RGB-space. The exact vector can be determined for a given light-spectrum and transfer-characteristics of the optical filters in the camera. It is shown that this "signature" can be used to design an rPPG algorithm with a much better motion robustness than the recent methods based on blind source separation, and even better than chrominance-based methods published earlier.

Motion robustness may further be enabled by the fact that subject motion typically modulates reflected light equally in all wavelengths (e.g. due to varying distance to the light-source, or changing orientation of the skin-surface with respect to the light-source), or in a direction complimentary to the skin-color (i.e. mostly bluish in RGB-color-space, when motion changes the fraction of specularly reflected light from the skin), while vital signs, e.g. the pulse, modulates some wavelengths (particularly green in RGB-color-space) relatively stronger than other wavelengths.

However, the obtained motion robustness is still considered insufficient in some critical applications. The reason for this is that the vital signs manifest themselves as very small color variations of the skin that are detected e.g. by a camera or a contact sensor. Subject motion, however, leads easily to much larger variations in the detected signals and recovering the vital sign from these severely distorted signals remains challenging.

XIONG JIPING ET AL: "Spectral Matrix Decomposition-Based Motion Artifacts Removal in Multi-Channel PPG Sensor Signals", IEEE ACCESS, vol. 4, pages 3076-3086, XP011615944, describes a multi-channel spectral matrix decomposition (MC-SMD) model to accurately estimate heart rate in the presence of intensive physical activities. Motivated by the observation that the PPG signal spectrum and the acceleration spectrum have almost the same spectral peak positions in the frequency domain, first the removal of motion artifacts is modelled as a spectral matrix decomposition optimization problem. After removing motion artifacts, a new spectral peak tracking method for estimating heart rate is proposed. Experimental results on the well-known PPG data sets recorded from 12 subjects during intensive movements demonstrate that MC-SMD can efficiently remove the motion artifacts and retrieve an accurate heart rate using multi-channel PPG sensor signals.

SUMMARY OF THE INVENTION

It is an object of the present invention to provide a device, system and method for obtaining a vital signal of a subject with improved robustness particularly against subject motion.

In a first aspect of the present invention a device for obtaining a vital signal of a subject is presented comprising:

an input unit for obtaining at least two detection signals acquired from a subject, the detection signals being related to a physiological property of the subject and allowing extraction of a vital sign of the subject, wherein detection signals are photoplethysmography, PPG, detection signals representing different wavelength intervals;

a decomposition unit for performing a spectral decomposition of the at least two detection signals to obtain two or more spectral components of the detection signals;

a weighting unit for determining a weight per spectral component based on an estimate of the relevance of the respective spectral component to the vital sign, based on a characteristic of said spectral component, and a vital sign extraction unit for obtaining a vital sign by i) weighting at least part of the spectral components with the determined corresponding weight and extracting a vital sign from the weighted spectral components or ii) extracting two or more vital sign sub-signals from individual spectral components of the at least two detection signals and, weighting the extracted vital sign sub-signals with the determined weight of the corresponding spectral component, and extracting a vital sign from the weighted vital sign sub-signals.

In a further aspect of the present invention a system for obtaining a vital signal of a subject is presented comprising:

a detection signal acquisition unit for acquiring at least two detection signals from a subject, the detection signals being related to a physiological property of the subject and allowing extraction of a vital sign of the subject; and a device as disclosed herein for obtaining a vital signal of the subject based on the acquired detection signals.

In yet further aspects of the present invention, there are provided a corresponding method, a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, system, computer program and medium have similar and/or identical preferred embodiments as the claimed device, in particular as defined in the dependent claims and as disclosed herein.

The present invention is based on the idea to considerably improve the performance of known solutions by weighting the spectral components using an estimate of the relevance of the respective spectral component to the vital sign, based on a characteristic of said spectral component. By spectrally decomposing the detection signals, this estimation of the relevance is exploited by suppressing or at least attenuating spectral components that cannot be explained by the respective physiological activity, e.g. by cardiac, or respiratory, activity in case of PPG signals. Thereafter, adapted detection signals are formed to which various techniques to further suppress motion-induced distortions may be applied. Hereby, the order of combining adapted detection signals and extraction of a vital sign can be reversed.

The proposed solution is thus different from other solutions which either use a fixed band-pass filter, where some spectral components receive a fixed low weight, or use an adaptive band-pass filter, in which only a narrow range of components around the pulse-rate is passed, and the other components are suppressed. In the latter case, the weight of all components is based on an estimate of the pulse frequency, and all other, or at least significantly different, frequency components are suppressed. In contrast, according to the present invention the relevance of a component is not determined by the estimated pulse frequency, but rather by a characteristic of the spectral component itself, particularly by the (relative) amplitude or energy of said component, or the relative strength of different combinations of corresponding components from different wavelength channels, as proposed in preferred embodiments.

Generally, in an embodiment, the weighting may be made such that the weight given to a less relevant spectral component is lower than the weight given to a more relevant spectral component.

According to a preferred embodiment said weighting unit is configured to use an estimate of the relevance that is based on the energy and/or amplitude of the respective spectral component and/or the relative strength of the spectral component in different combinations of the at least two detection signals, wherein the relevance of a spectral component is determined as an increasing or decreasing function of the amplitude, energy or relative strength. Thus, according to this embodiment the amplitude and/or energy and/or relative strength of spectral components of the obtained detection signals (e.g. PPG signals acquired by a contact sensor attached to the skin or by a camera pointed at the skin in an exemplary embodiment) is used as a kind of prior knowledge. By spectrally decomposing the detection signals, this prior knowledge is exploited by suppressing or at least attenuating spectral components with an amplitude and/or energy and/or relative strength in parallel wavelength channels that cannot be explained by the respective physiological activity, e.g. by cardiac activity in case of PPG signals.

In an embodiment, said weighting unit is configured to determine a weight of a spectral component such that it is lower, the higher the energy and/or amplitude is, or that it is lower or higher depending on the definition and value of the relative strength of the respective spectral component (at least from a certain threshold value onwards). This allows a more accurate determination of the weights and suppression of spectral components not related to the desired vital. Preferably, the gain for a spectral component is not increased much further when it is very small as this would imply that sensor noise would be amplified. The effect of the spectral component shall be reduced if there are indications that it cannot be a vital sign because its amplitude or energy is way too high for that or its relative amplitude in the different color channels indicate that it unlikely is a pulse signal. In an embodiment a relative strength of two linear combinations of the spectral component in different wavelength channels may thus be considered. In the numerator a linear combination that reflects total energy (pulse+motion) may be put, and in the denominator a linear combination that aims at suppressing the motion and keeping the pulse may be put. If the relative strength is high, it is likely distortion component (and the gain of this component is reduced). If it is relatively low, it is likely pulse and a high gain of the spectral component is kept.

According to another embodiment said weighting unit is configured to determine the weight such that a weight of a spectral component having an energy and/or amplitude above a threshold is lower than the weight of a spectral component having an energy and/or amplitude below the threshold or that the weight of a spectral component having a higher relative strength is lower than the weight of the same spectral component of another detection signal. Hereby, as threshold an expected energy and/or amplitude or a predetermined energy and/or amplitude of the respective spectral component or a predetermined or expected relative strength of different combinations of corresponding spectral components from the detection signals may be used. Thus, depending on the vital sign to be extracted different thresholds may be used. Further, the thresholds may also be set based on information about the subject, e.g. age, weight, size, health status, etc.

According to a preferred embodiment said weighting unit is configured to combine, per detection signal, at least part of the weighted spectral components into adapted detection signals and said vital sign extraction unit is configured to extract the vital sign from the adapted detection signals. The combination may e.g. be an averaging. This embodiment further improves the accuracy of the vital sign extraction.

The spectral decomposition unit may be configured to perform one of a Fourier analysis, a sub-band decomposition, a singular spectrum analysis, a multi-channel singular spectrum analysis, and an empirical mode decomposition. The different methods all split the signal into multiple components where each component is typically characterized by a central frequency. The Fourier analysis and subband decomposition are prefixed operations, typically providing a large number of components. Due to the pre-defined analysis character, the actual component of interest may be split across multiple components. The other methods are data-driven decompositions computationally more demanding and typically give a more limited number of components (or can be restricted in this way). There is thus a trade-off between number of components, risk of splitting the pulse signal (component of interest) and computational costs.

In a particular field of application the detection signals include at least two photoplethysmography, PPG, detection signals representing different wavelength intervals and wherein said weighting unit is configured to determine the identical weight for the same spectral components of different detection signals in case the spectral components have the same energy and/or amplitude. The PPG detections signals may be acquired by a contact sensor (e.g. pulse oximeter) or a non-contact sensor (e.g. an imaging unit such as a vital signs camera).

The input unit may be configured to obtain at least three input detection signals (e.g. RGB signals for different color channels, for instance acquired by an RGB camera, but the color channels may also completely, or partially, be selected from the near infrared (NIR) spectrum) and the device may further comprise a pre-processing unit for combining the input detection signals into said at least two detection signals (e.g. x- and y-signals, x and y representing the axes on a chrominance plane in color space).

Preferably, said pre-processing unit is configured to combine the input detection signals by a linear combination of temporally normalized input detection signals. Hereby, different linear combinations may be used. Instead of a temporal normalization, also a logarithmic transfer function may be applied to the input detection signals.

In another embodiment the vital sign extraction unit is configured to project corresponding spectral components from different (temporally normalized or logarithmic) detection signals on a projection axis. An axis in a color space of e.g. three color detection signals (R, G, B) can be defined as a linear combination of the three color detection signals. For instance, $1R+0G+0B$ equals the R-axis, and $0.5R+0.5G+0B$ is a diagonal axis in the RG-plane (B=0). Extraction of the pulse signal, P, by projecting on an axis in RGB-space, means $P=w1 \cdot R+w2 \cdot G+w3 \cdot B$, where the weights wi are selected to maximally suppress the (motion-induced) distortions. In the above R may be the temporally normalized $R/\sigma(R)$ (where $\sigma(R)$ is the temporal mean of R), or also $\log(R)$.

The weighting unit may further be configured to determine a weight by determining the variance or standard deviation of the respective spectral component and by keeping the weight at value 1, unless the variance or standard deviation is above a predetermined or expected limit. This provides a rather simple way of determining the weights.

In another embodiment said weighting unit is configured to determine a gain G as weight by determining $G=1/(var+bias)$, wherein the parameter bias is selected such that the gain G is substantially stable when var, representing the variance or standard deviation or relative strength, is lower than a predetermined or expected limit, and that the gain G is decreasing when var is above the predetermined or expected limit. The gain G may particularly drop rapidly when the variance or standard deviation or relative strength (var) is above the predetermined or expected limit.

For acquiring the detection signals various options exist, i.e. the present invention may generally be applied in many different fields with different kinds of detection signals. Hence, the detection signal acquisition unit may be configured to generate as detection signals one of the following types of detection signals:

i) photoplethysmography signals obtained from radiation transmitted through or reflected from a subject's body part in response to radiation incident on the body part;

ii) motion signals representing motion of at least a subject's body part;

iii) electrical signals representing an electrically measurable physiological parameter of the subject.

According to another aspect of the present invention a device and a corresponding method are present, wherein the device comprises an input unit for obtaining at least two detection signals acquired from a subject, the detection signals being related to a physiological property of the subject and allowing extraction of a vital sign of the subject;

a decomposition unit for performing a spectral decomposition of the at least two detection signals to obtain two or more spectral components of the detection signals;

a weighting unit for determining a weight per spectral component based on the energy and/or amplitude of the respective spectral component and/or the relative strength of (different combinations of) the spectral component in the at least two detection signals, wherein the weight of a spectral component having an energy and/or amplitude above a threshold is lower than the weight of a spectral component having an energy and/or amplitude below the threshold or wherein the weight of a spectral component having a higher relative strength is lower than the weight of the same spectral component of another detection signal; and a vital sign extraction unit for obtaining a vital sign by i) weighting at least part of the spectral components with the determined corresponding weight and extracting a vital sign from the weighted spectral components or ii) extracting two or more vital sign sub-signals from individual spectral components of the at least two detection signals and, weighting the extracted vital sign sub-signals with the determined weight of the corresponding spectral component, and extracting a vital sign from the weighted vital sign sub-signals.

BRIEF DESCRIPTION OF THE DRAWINGS

These and other aspects of the invention will be apparent from and elucidated with reference to the embodiment(s) described hereinafter. In the following drawings FIGS. 4A-E show diagrams illustrating the signals at various steps of the processing using absolute weighting.

DETAILED DESCRIPTION OF THE INVENTION

Figure 1:
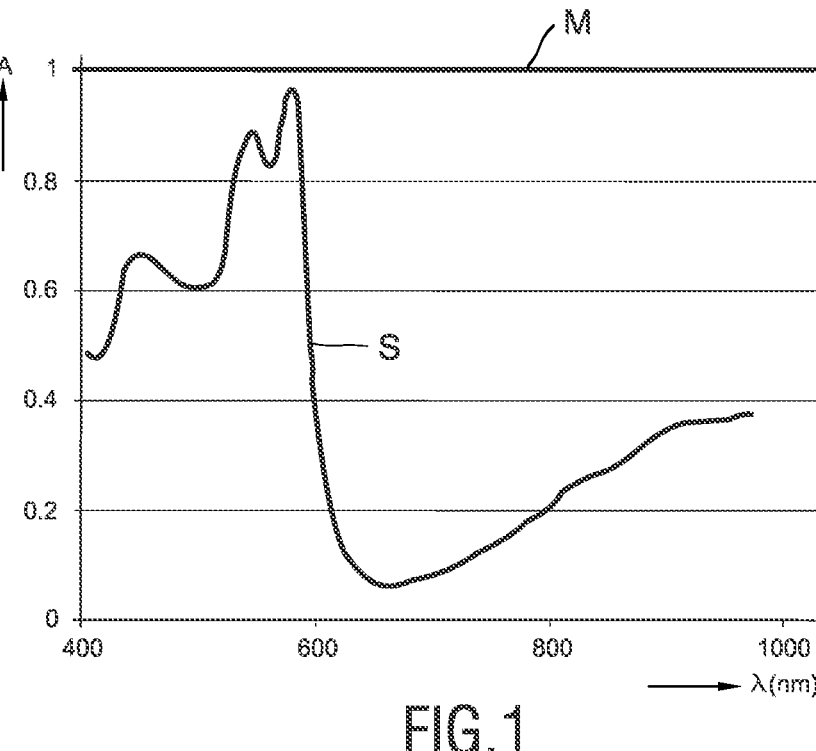
FIG. 1 shows a diagram illustrating the relative PPG amplitude over wavelength.

FIG. 1 shows a diagram illustrating the relative PPG amplitude over wavelength. As can be seen from this diagram, the relative PPG amplitude S depends strongly on the wavelength of the light reflected from the skin of a subject. In contrast, the relative signal strength M caused by motion is completely wavelength independent. Thus, basic motion robustness is enabled by the fact that subject motion modulates the reflected light equally in all wavelengths, while vital signs, e.g. the pulse, modulates some wavelengths relatively stronger than other wavelengths. However, to obtain improved robustness particularly against subject motion further measures have to be taken.

Figure 2:
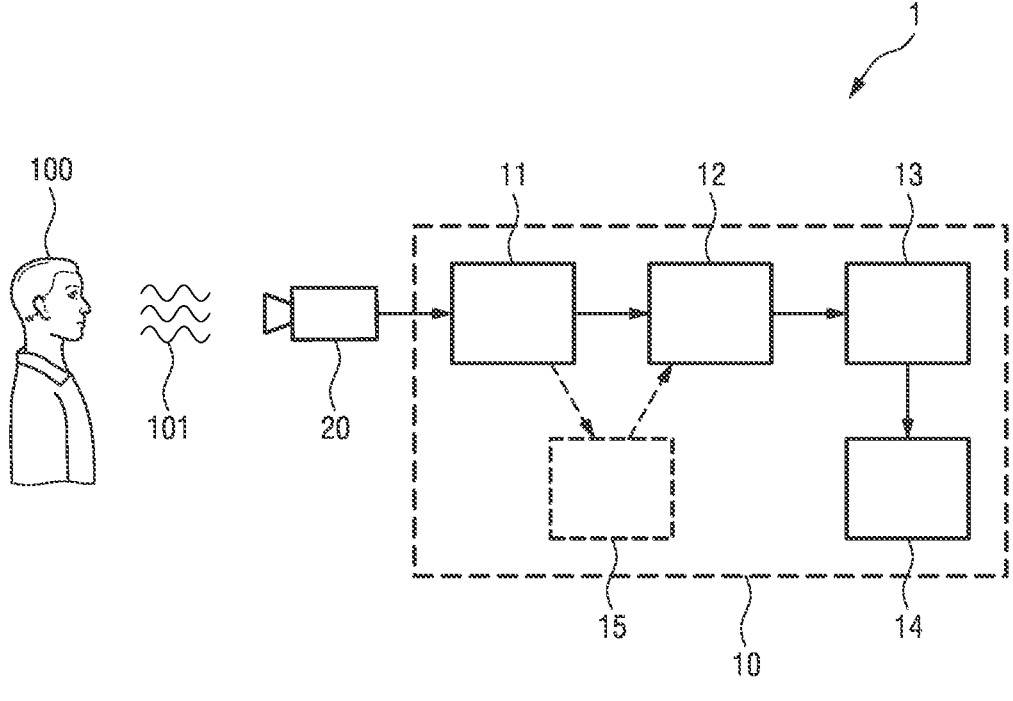
FIG. 2 shows a schematic diagram of a first embodiment of a system and device according to the present invention.

FIG. 2 shows a schematic diagram of a first embodiment of a system 1 and device 10 according to the present invention. The system 1 generally comprises a detection signal acquisition unit 20 for acquiring at least two detection signals from a subject 100, the detection signals being related to a physiological property of the subject and allowing extraction of a vital sign of the subject. Further, the system 1 comprises a device 10 for obtaining a vital signal of the subject based on the acquired detection signals.

The signal acquisition unit 20 in this embodiment comprises an imaging unit, such as a camera, receiving radiation 101 (in particular light) from the subject 100, e.g. a person or patient. Such an imaging unit is generally known in the art of remote PPG and may be regular RGB camera, web cam, video camera, etc.

The device 10 may be implemented in hard- and/or software, e.g. a programmed processor or computer or corresponding circuitry. The device 10 comprises an input unit 11 for obtaining at least two detection signals acquired from the subject by the imaging unit. The input unit 11 may e.g. be a data interface for receiving or retrieving the detection signals from the imaging unit 11 in a wired or wireless manner.

The device 10 further comprises a decomposition unit 12 for performing a spectral decomposition of the at least two detection signals to obtain two or more spectral components of the detection signals. The spectral decomposition can be a sub-band decomposition, e.g. a Fourier transform, but data-driven decompositions, like (Multi-channel) Singular Spectrum Analysis (SSA and MSSA), or an Empirical Mode Decomposition (EMD), have been shown to be particularly attractive.

The device 10 further comprises a weighting unit 13 for determining a weight per spectral component based on an estimate of the relevance of the respective spectral component to the vital sign, wherein the weight given to a less relevant spectral component is lower than the weight given to a more relevant spectral component. The weight thus determines the contribution of the spectral components to the output vital sign For instance, the weights of the respective spectral components are determined such that it decreases rapidly with increasing energy/amplitude of spectral components with a relatively high (e.g. compared to the expected energy/amplitude of the vital signal) energy/amplitude and varies only little for components with a relatively low energy/amplitude.

The device 10 further comprises a vital sign extraction unit 14 for obtaining a vital sign, in particular by combining signals from different detection signals. Hereby, various options exist. In one option, at least part of the spectral components is weighted with the determined corresponding weight and a vital sign is extracted from the weighted spectral components. In an alternative option, two or more vital sign sub-signals are first extracted from individual spectral components of the at least two detection signals, then the extracted vital sign sub-signals are weighted with the determined weight of the corresponding spectral component, and finally a vital sign is extracted from the weighted vital sign sub-signals. The extraction may involve a(n) (adaptive) projection much similar to what has been described in G. de Haan and V. Jeanne, "Robust pulse-rate from chrominance-based rPPG", IEEE, Tr. On Biomedical Engineering, Vol. 60, No. 10, October, 2013, pp. 2878-2886. More details and preferred embodiments will be described below.

In some embodiments more than two detection signals at different wavelengths may be used, e.g. red, green and blue channels from a camera 20 as shown in FIG. 2. Accordingly, in such embodiments a pre-processing unit 15 may optionally be provided for combining the input detection signals into said at least two detection signals, in particular by a linear combination of temporally normalized (or logarithmic versions of) input detection signals. For instance, in a pre-processing step three input detection signals may be combined to fewer detection signals (X, Y, e.g. representing two axes on a chrominance-plane in color space), that are consequently input to the decomposition unit 12. The advantage of this step is that the processing demands are reduced because fewer detection signals have to be spectrally decomposed and processed. In essence, this can also be interpreted as if the pulse extraction is split over a pre-processing (projection to chrominance-plane) and a post-extraction (only an adaptive weighting of the remaining channels is still necessary).

Further, in the previous embodiment the derived detection signals from the pre-processing typically include different linear combinations of temporally normalized (or logarithmic) (r)PPG input detection signals (e.g. X=a1Rn+b1Gn+ c1Bn, Y=a2Rn+b2Gn+c2Bn, with ai+bi+ci=0).

Figure 3:
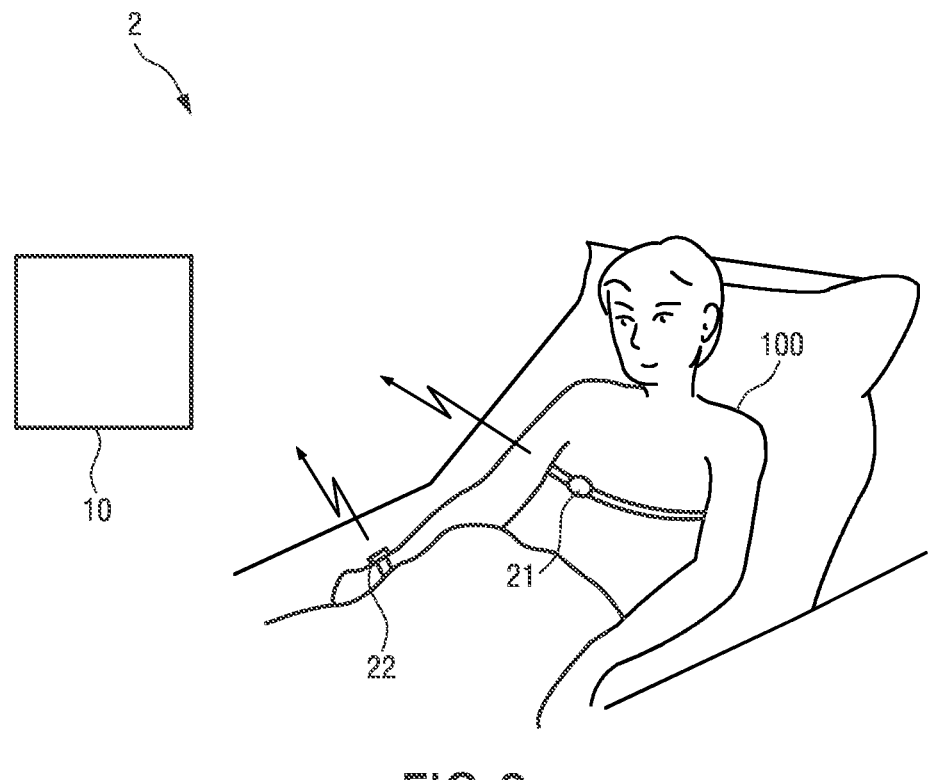
FIG. 3 shows a schematic diagram of a second embodiment of a system according to the present invention.

FIG. 3 shows a schematic diagram of a first embodiment of a system 2 according to the present invention. The system 2 comprises a device 10 of the same kind as shown in FIG. 2. Further, the detection signal acquisition unit comprises contact sensor 21, in particular a pulse oximeter, in this embodiment mounted to the subject's body by a belt, but it can also e.g. be a finger pulse oximeter (e.g. a finger clip). The detection signals acquired by the contact sensor 21 are photoplethysmography signals obtained from radiation reflected from (or alternatively transmitted through) a subject's body part in response to radiation incident on the body part.

In both embodiments shown in FIGS. 2 and 3, two PPG detection signal may be available, e.g. the red and infrared channels of a finger-oximeter or a camera registering an area of skin from which the average pixels values for each wavelength are used. In a particular embodiment of the device 10, both detection signals are filtered, e.g. with complementary filters in the pulse-rate band, to obtain at least two spectral components per detection signal. The amplitude/energy in each spectral component is measured, from which a gain factor for said spectral component is determined, such that the component is suppressed if the amplitude/energy is higher than what is expected from said wavelength channel for the pulse-signal. Next the weighted spectral components are combined (averaged) per wavelength signal to obtain adapted detection signals. Consequentially, these adapted detection signals are input to the pulse extraction, from which the output pulse-signal is typically obtained as a weighted average (i.e. projection on an axis in color space).

In an alternative embodiment, the pulse extraction may be performed on the corresponding spectral components of the different detection signals, prior to the weighting and summing. This allows individual projection axes for the different spectral components.

In case of using the energy and/or amplitude of the spectral components, the energy of a detection signal, e.g. the one with the lowest pulse-energy, is used to determine the strength of the distortions in a spectral component. If this is high, this spectral component may be considered as less relevant to the vital sign.

Generally, a PPG signal results from variations of the blood volume in the skin. Hence the variations give a characteristic pulsatility "signature" when viewed in different spectral components of the reflected/transmitted light. This "signature is basically resulting as the contrast (difference) of the absorption spectra of the blood and that of the blood-less skin tissue. If the detector, e.g. a camera or sensor, has a discrete number of color channels, each with a different spectral sensitivity, e.g. each sensing a particular part of the light spectrum, then the relative normalized pulsatilities, i.e. the ratio of the relative pulsatilities, in these channels can be arranged in a "signature vector", also referred to as the "normalized blood-volume vector", Pbv. It has been shown G. de Haan and A. van Leest, "Improved motion robustness of remote-PPG by using the blood volume pulse signature", Physiol. Meas. 35 1913, 2014, which is herein incorporated by reference, that if this signature vector is known then a motion-robust pulse signal extraction on the basis of the color channels and the signature vector is possible. For the quality of the pulse signal it is essential though that the signature is correct, as otherwise the known methods mixes noise into the output pulse signal in order to achieve the prescribed correlation of the pulse vector with the normalized color channels as indicated by the signature vector. Details of the Pbv method and the use of the normalized blood volume vector (called "predetermined index element having a set orientation indicative of a reference physiological information") have also been described in US 2013/ 271591 A1, which details are also herein incorporated by reference.

There exist several known methods besides Pbv to obtain a pulse signal S from (normalized) detection signals, said methods being referred to as ICA, PCA, CHROM, and ICA/PCA guided by Pbv/CHROM, which have also been described in the above cited paper of de Haan and van Leest. These methods can be interpreted as providing the pulse signal as a mixture of different wavelength channels, e.g. red, green and blue signals from a color video camera, but they differ in the way to determine the optimal weighting scheme. In these methods the resulting weights are aimed at a mixture in which the distortions disappear, i.e. the "weighting vector" is substantially orthogonal to the main distortions usually caused by subject motion and/or illumination variations.

In an alternative embodiment, possibly in addition to a PPG detection signal, a motion detection signal is added. This may be from an accelerometer 22 (see FIG. 3), e.g. included in the finger-oximeter, or from a video motion-estimator in case a video camera is used as the PPG sensing device.

In yet an alternative embodiment, electrical input detection signals may be used, like e.g. ECG-signals, EMG-signals, or signals from a thoracic volume measurement (e.g. acquired by a respiband).

In a more advanced embodiment, many more spectral components may be generated from the individual detection signals, e.g. by performing a Fourier transform (FT), a sub-band decomposition (SB), a (possibly multi-channel) singular spectrum analysis (SSA, MSSA), an empirical mode decomposition (EMD), etc. After decomposition again the weights are computed depending on the amplitude/ energy of each spectral component, etc.

In a further advantageous embodiment, the weights of corresponding spectral components in different wavelength detection signals are jointly computed and the same weight is applied to corresponding components. The advantageous consequence here is that the relative pulse-amplitude in the different wavelength channels will not be modified, which is a prerequisite for most extraction methods (e.g. POS, CHROM, PBV).

Rather than limiting the var of the spectral components as described above, the gain advantageously may be computed by G=1/(var+bias), where the bias is selected such that the gain is nearly stable when var is lower than the estimated var of the pulse-signal, but quickly drops when it is higher.

Other variants are $G=b^m/(v^m+b^m)$, where b denotes the bias, v the variance and m is the power coefficient, with $m>\frac{1}{2}$. With $m>1$, there is a stronger suppression of the high-amplitude signals then with the earlier given expression. Yet another option would be $G=(bv)^{m/2}/(v^m+b^m)$. Here a suppression of both high and low amplitude signals is obtained; signals with variance close to b are least attenuated.

In another embodiment the weighting unit 13 is configured to use the relative strength of the spectral component in different combinations of the at least two detection signals, wherein the relevance of a spectral component is determined as an increasing or decreasing function of the relative strength. In case of using the relative strength of the spectral components, the strength in a combination that is expected to suffer little from known distortions (e.g. projection on axis orthogonal to intensity variations and specular reflection distortions: C1=var(−R+2G−B)) is compared with the strength in a combination that suffers significantly from known distortions (could be total (sum) energy in the detection signals: C2var(R+G+B)). The lower this ratio C1/C2, the less important this spectral component may be considered for the vital sign.

FIGS. 4A to 4E show diagrams illustrating the signals at various steps of the processing using absolute weighting. FIG. 4A shows the three color signals from an RGB camera. FIG. 4B shows the spectral components of the three color signals showing a peak P1 resulting from motion and another peak P2 resulting from pulse. FIG. 4C shows the weighting (determined for the red color signal only) based on the amplitude of the spectral components of the red color signal. As can be seen, spectral components having an amplitude below approx. 0.002 (i.e. including the peak P2 caused by pulse having a lower amplitude) are weighted by 1, whereas spectral components having an amplitude above approx. 0.002 (i.e. including the peak P1 caused by motion having a higher amplitude) are weighted by 0. FIG. 4D shows the filtered spectral signals (i.e. the spectral signals shown in FIG. 4B after application of the weights). FIG. 4E shows the corresponding filtered color signals, which are then used for extraction of the vital sign.

Figure 5A:
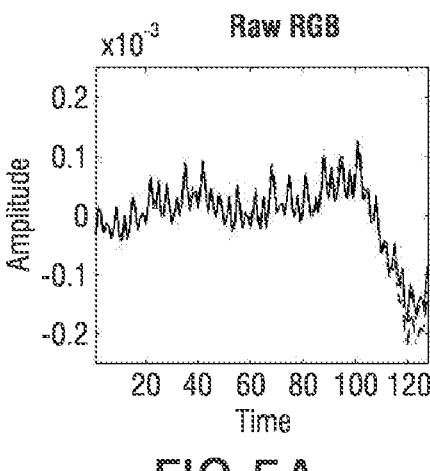
FIGS. 5A-F show diagrams illustrating the signals at various steps of the processing using relative weighting.
Figure 5B:
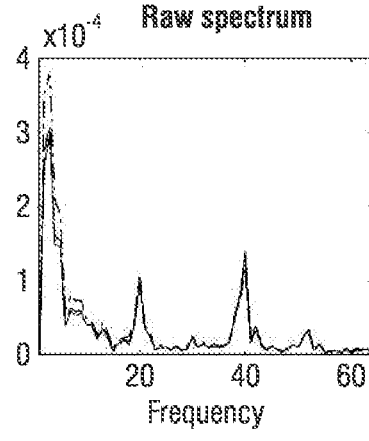
Figure 5C:
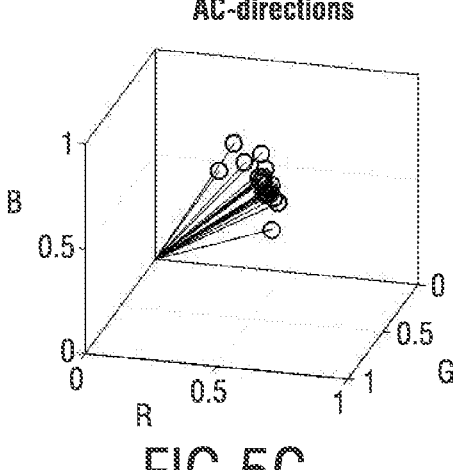

FIGS. 5A to 5F show diagrams illustrating the signals at various steps of the processing using relative weighting. FIG. 5A shows the three color signals from an RGB camera. FIG. 5B shows the spectral components of the three color signals showing two peaks P3 and P4 resulting from motion. FIG. 5C shows the weighting based on the relative strength of the spectral components. The relative strength of a spectral component in R, G, and B direction can be represented as a vector (a direction) in the (normalized or logarithmic) RGB color space. Directions indicate whether a component contains mostly motion-induced distortions, or contains significant pulse. Depending on the actual direction of a component the weight can be decreased if it suggests mostly distortion energy. The weights not necessarily have to be determined directly from the direction in color space.

Figure 5D:
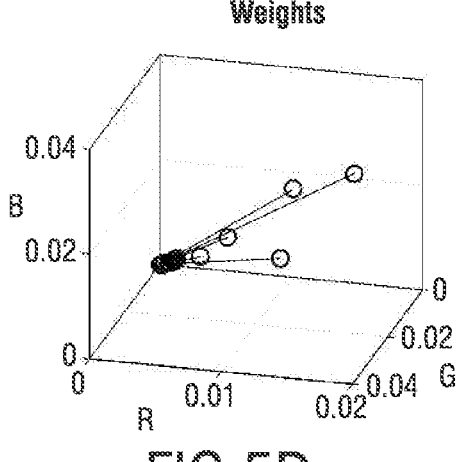
Figure 5E:
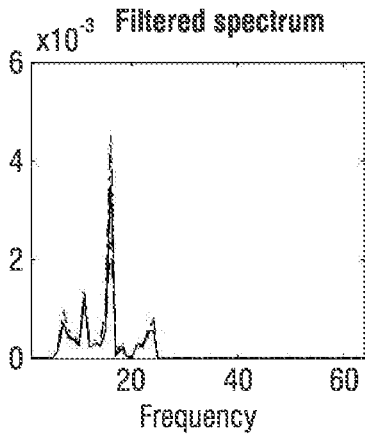
Figure 5F:
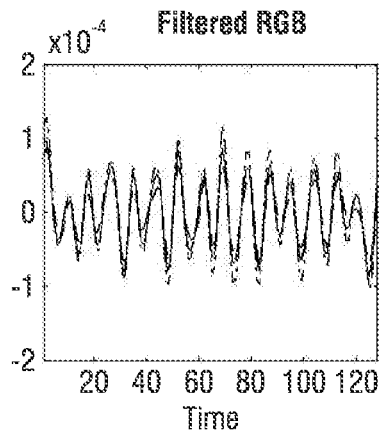

Instead, in an advantageous embodiment the corresponding spectral components from different wavelength channels may first be combined in different ways (projection of the data onto different lines), and the relative strength of these differently combined signals may then be used to determine the weights. Preferably, two combinations may be used, where the first represents the total amplitude/energy and the other predominantly the pulse-related energy (e.g. by projecting onto a line orthogonal to intensity and specular reflection variations). The illustration in FIGS. 5C and 5D show different spectral components before and after weighting. Each component is characterized by its relative energies in RGB-space (a vector) and the result of weighting is that some vectors shrink (the spectral component gets a lower weight) because their relative energies seem to indicate a lower relevance for the vital sign (a higher chance that they are reflecting distortions). FIG. 5E shows the filtered spectral signals (i.e. the spectral signals shown in FIG. 5B after application of the weights). FIG. 5F shows the corresponding filtered color signals, which are then used for extraction of the vital sign.

The present invention may advantageously be applied in the camera-based measurement of pulse-rate, respiration and SpO2 for patient monitoring. The contactless monitoring, with a camera, is assumed to be highly relevant for premature babies with very sensitive skin in NICUs, and for patients with damaged (e.g. burns) skin, but may also be more convenient than contact sensors as used in the general ward. The invention is expected to be equally applicable to currently popular contact sensors though.

The present invention focusses on using the spectral component weighting to suppress the components that are not belonging to a pulse (e.g., motion components). The input can be 1D PPG signal. In addition, this technique can be used to select the PPG signal from a multi-site measurement. While known methods use Blind Source Separation (BSS) like independent component analysis (ICA) or principal components analysis (PCA) to select one signal component from multiple (or spatially redundant) measurements, the present invention uses spectral weighting to select/combine the pulse-related frequency component from multiple measurements, which is typically useful for the full-video pulse measurement.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for obtaining a weighted vital signal of a subject, the device comprising:

an input unit for obtaining at least two detection signals acquired from a subject, the detection signals being related to a physiological property of the subject and allowing extraction of a vital sign of the subject;

a decomposition unit for performing a spectral decomposition of the at least two detection signals to obtain two or more spectral components of the detection signals;

a weighting unit for determining a weight per spectral component based on an estimate of the relevance of a spectral component to the vital sign, derived from a characteristic of the spectral component, wherein the weighting unit is configured to:

determine a weight by determining at least one of a variance of the spectral component and a standard deviation of the spectral component, determine whether at least one of the variance and the standard deviation exceed a predetermined limit, and responsive to determining that at least one of the variance and the standard deviation do not exceed the predetermined limit, setting the weight to a weight value of 1; and a vital sign extraction unit for extracting the weighted vital sign.

2. The device of claim 1, wherein the at least two detection signals are selected from the group consisting of: photoplethysmography (PPG) signals, electrical input detection signals, motion detection signals, and individual detection signals.

3. The device of claim 1, wherein the vital sign extraction unit is further configured to apply at least one weight to at least one spectral component with the weight and extract a vital sign from the weighted spectral components.

4. The device of claim 1, wherein the vital signal extraction unit is further configured to:

extract two or more vital sign sub-signals from individual spectral components of the at least two detection signals, weight the extracted vital sign sub-signals with the determined weight of the corresponding spectral component, and extract a vital sign from the weighted vital sign sub-signals.

5. The device according to claim 1, wherein the weighting unit is further configured to use an estimate of the relevance, wherein the relevance is based on (1) at least one of an energy and an amplitude of the spectral component and (2) at least one of a relative strength of the spectral component in different combinations of the at least two detection signals, and wherein the relevance of the spectral component is determined as an increasing or decreasing function of at least one an amplitude, an energy, and a relative strength.

6. The device according to claim 5, wherein the weighting unit is further configured to:

determine whether at least one of the energy and the amplitude of the spectral component exceeds a threshold, responsive to determining that at least one of the energy and the amplitude of the spectral component exceeds a threshold, lower the weight value.

7. The device of claim 5, wherein the weighting unit is further configured to:

determine a definition and a value of the relative strength of different combinations of the spectral component, and responsive to determining the definition and the value of the relative strength in different combinations of the respective spectral component, adjust the weight value.

8. The device according to claim 5, wherein the weighting unit is further configured to determine the weight such that a weight of a spectral component having at least one of an energy and an amplitude above a threshold is lower than a weight of the spectral component having at least one of an energy and an amplitude below the threshold or that the weight of a spectral component having a higher relative strength in a particular combination is lower than the weight of the same spectral component of another combination of detection signals, in particular using as threshold an expected energy and/or amplitude or a predetermined energy and/or amplitude of the respective spectral component or a predetermined or expected relative strength of different combinations of corresponding spectral components from the detection signals.

9. The device according to claim 1, wherein the weighting unit is further configured to:

combine, per detection signal, one or more weighted spectral components into adapted detection signals, and extract the vital sign from the adapted detection signals.

10. The device according to claim 1, wherein the spectral decomposition unit is further configured to perform at least one of a Fourier analysis, a sub-band decomposition, a singular spectrum analysis, a multi-channel singular spectrum analysis, and an empirical mode decomposition.

11. The device according to claim 1, wherein the weighting unit is further configured to determine an identical weight for corresponding spectral components of different detection signals responsive to determining that the corresponding spectral components have at least one of a same energy and a same amplitude.

12. The device according to claim 1, wherein the input unit is further configured to:

obtain at least three input detection signals, and wherein the device further comprises a pre-processing unit, wherein the pre-processing unit is configured to combine input detection signals into the at least two detection signals using a linear combination of at least one of a temporally normalized version or logarithmic version of the input detection signals.

13. The device according to claim 1, wherein the vital sign extraction unit is further configured to project corresponding spectral components from different detection signals on a projection axis.

14. The device according to claim 1, wherein the weighting unit is further configured to determine a gain G as weight by determining $G=1/(var+bias)$, wherein the parameter bias is selected such that the gain G is substantially stable when var, representing at least one of the variance, the standard deviation, and the relative strength, is lower than a predetermined or expected limit, and the gain G is decreasing when var is above the predetermined limit.

15. A method for obtaining a weighted vital signal of a subject, said method comprising:

obtaining at least two detection signals acquired from a subject, the detection signals being related to a physiological property of the subject and allowing extraction of a vital sign of the subject;

performing a spectral decomposition of the at least two detection signals to obtain two or more spectral components of the detection signals;

determining a weight per spectral component based on an estimate of the relevance of the spectral component to the vital sign, wherein determining the weight of the spectral component further comprises deriving the weight from a characteristic of the spectral component by:

determining a weight value by determining at least one of a variance of the spectral component and a standard deviation of the spectral component, and determining whether at least one of the variance and the standard deviation exceed a predetermined limit, and responsive to determining that at least one of the variance and the standard deviation do not exceed the predetermined limit, setting the weight to a weight value of 1; and extracting the weighted vital sign of the subject.

16. The method of claim 15, further comprising applying at least one weight to at least one spectral component with the weight and extracting a vital sign from the weighted spectral components.

17. The method of claim 15, further comprising;

extracting two or more vital sign sub-signals from individual spectral components of the at least two detection signals, weighting the extracted vital sign sub-signals with the determined weight of the corresponding spectral component, and extracting a vital sign from the weighted vital sign sub-signals.

18. The method of claim 15, wherein the at least two detection signals are selected from the group consisting of: photoplethysmography (PPG) signals, electrical input detection signals, motion detection signals, and individual detection signals.

19. The method of claim 15, wherein the relevance is based on (1) at least one of an energy and an amplitude of the spectral component and (2) at least one of a relative strength of the spectral component in different combinations of the at least two detection signals, and wherein the relevance of the spectral component is determined as an increasing or decreasing function of at least one an amplitude, an energy, and a relative strength.

20. The method of claim 15, further comprising;

determining whether at least one of the energy and the amplitude of the spectral component exceeds a threshold, responsive to determining that at least one of the energy and the amplitude of the spectral component exceeds a threshold, lowering the weight value.

* * * * *